United States Patent [19]

Lamberti et al.

[11] 4,132,735

[45] Jan. 2, 1979

[54] DETERGENT COMPOSITIONS

[75] Inventors: Vincent Lamberti, Upper Saddle River; Chester R. Willis, Mapleshade, both of N.J.

[73] Assignee: Lever Brothers Company, New York, N.Y.

[21] Appl. No.: 880,666

[22] Filed: Feb. 23, 1978

Related U.S. Application Data

[60] Continuation of Ser. No. 591,220, Jun. 27, 1975, Pat. No. 4,095,035, which is a division of Ser. No. 461,060, Apr. 15, 1974, Pat. No. 3,922,230, which is a continuation of Ser. No. 169,101, Aug. 4, 1971, abandoned.

[51] Int. Cl.$^2$ ............................................. C07C 59/22
[52] U.S. Cl. .................................. 562/582; 562/590; 562/594
[58] Field of Search ..................................... 260/535 P

[56] References Cited

U.S. PATENT DOCUMENTS

| | | | |
|---|---|---|---|
| 3,914,297 | 10/1975 | Lamberti | 260/535 P |
| 3,994,969 | 11/1976 | Vanlautem | 260/535 P |
| 4,066,687 | 1/1978 | Nelson | 260/535 P |

*Primary Examiner*—Paul J. Killos
*Attorney, Agent, or Firm*—Michael J. Kelly; James J. Farrell; Melvin H. Kurtz

[57] ABSTRACT

The present invention relates to a novel class of oligomeric builders for use in detergent compositions. More particularly, the present invention relates to a biodegradable, oligomeric polyacrylate having a molecular weight of greater than about 500 and less than about 10,000, preferably less than about 5000. In the most desirable embodiments at least one end of the oligomer chain is terminated with either a sulfur containing moiety or an hydroxy containing moiety. Preferred cations are alkali metals, ammonium and substituted ammonium.

1 Claim, No Drawings

DETERGENT COMPOSITIONS

This is a continuation of application Ser. No. 591,220 filed June 27, 1975, now U.S. Pat. No. 4,095,035, which is a division of Ser. No. 461,060, filed Apr. 15, 1974 now U.S. Pat. No. 3,922,230, which is a continuation of Ser. No. 169,101 filed Aug. 4, 1971, abandoned.

BACKGROUND OF THE INVENTION

1. Field of The Invention

Non-phosphorus oligomeric biodegradable builders for detergent compositions.

2. Description of the Prior Art

In recent years the problems of eutrophication, which can be defined as a slow rate, natural process of enrichment of waters with nutrients, such as phosphorus and nitrogen has received much notoriety. Uncontrolled or pronounced eutrophication has been found to cause increased algal growth and algal scums which not only are unaesthetic, odorous, distasteful and clog filters or treatment plants but also creates disproportionate demands on the available oxygen in the water. It has been postulated that in several bodies of water various human activities have contributed to acceleration of the process through such factors as inordinate enrichment of natural runoff, ground water and agricultural drainage, sewage and waste effluents. It has also been suggested that the phosphorus-containing builders present in detergent compositions can be contributing factor in eutrophication, and therefore any substitutes which do not contain phosphorus may decrease to some extent the eutrophication problem. Thus, those skilled in the art have expended a great deal of time and money to solve this problem and find suitable materials to reduce or replace the existing phosphate builders in detergent compositions. This work is still continuing since most of the builders discovered to date have been deemed unsatisfactory for a variety of reasons and are most often less efficient than the existing phosphate builders.

High molecular weight acrylate polymers have been known in the art for many years, finding significant use as molding resins, films and fibers. Particular species of the higher molecular weight acrylate polymers, such as sodium polyacrylates in British Pat. No. 1,090,809 and alpha halogen substituted polyacrylates such as polyalpha chloracrylic acid, polyalpha fluoracrylic acid and copolymers thereof with other polymerizable organic compounds, in U.S. Pat. No. 2,327,302 have been suggested as capable of functioning as detergent assistants. These compounds, however, create as much, if not more, of a problem than they ostensibly solve since at the molecular weight of the polymers believed contemplated by these patents, the molecules would not be biodegradable.

A large proportion of the sanitary treatment performed in this country is done aerobically. If the bacteria in the degradation system cannot consume and degrade a molecule it may pass through the tank and flow into the surrounding area, ultimately mixing with the surface water and eventually becoming part of the human water supply. It has been found that, bacteria either cannot or have extreme difficulty in degrading long chain polymers and branched polymers of the type disclosed in the above patents. Since so little is known about the effects of so many chemicals, particularly from a carcinogenic and birth defects standpoint, when ingested by human beings, a compound intended for use in a detergent formulation must be biodegradable or it is dropped from further consideration. As such, the compounds of British Pat. No. 1,090,809 and of U.S. Pat. No. 2,327,302, as well as other relatively high molecular weight polyacrylates would be deemed unacceptable for use in a detergent formulation.

SUMMARY OF THE INVENTION

It is therefore an object of the present invention to provide novel biodegradable builder compounds which are free of phosphorus and can be incorporated into detergent compositions.

The compositions of the invention necessarily include both a synthetic builder and a water-soluble organic detergent compound; such as the anionic (soap and non-soap), nonionic, zwitterionic and ampholytic detergent compounds. The chemical nature of these detergent compounds is not an essential feature of the present invention, since these are well known to those skilled in the detergent art and the literature is replete with disclosures of such compounds. Typical of such literature are "Surface Active Agents" by Schwartz and Perry and "Surface Active Agents and Detergents" by Schwartz, Perry and Berch, both of which are published by Interscience Publishers, Inc., New York, N.Y., the disclosures of which are incorporated herein by reference.

The phosphorus-free builders for the detergent compositions of the present invention are the alkali metal, ammonium and substituted ammonium salts of low molecular weight polyacrylic and polyalkylacrylic acid. More particularly, the polymers have an average molecular weight of between about 500 to about 10,000 with a preferred range of less than about 5000 and a most preferred range of less than about 3000.

DETAILED DESCRIPTION OF THE INVENTION

As discussed above the search for a phosphorus-free detergent builder composition has engendered a great deal of effort and expense on the part of the detergent industry. Basically, the criteria that a new builder must meet, aside from being free of phosphorus, are, first, that when incorporated into a detergent formulation, the resultant detergent efficiency of the formulation is equal to or closely approximates that of a similarly formulated, phosphorus built detergent; and, second, that the builder be biodegradable. As to the first requirement, it is axiomatic that a replacement for an established product must be at least as good as the established product if it is to gain any consumer acceptance. The second requirement is a result of the large proportion of aerobic sanitary treatment facilities in this country. Any possibility that a compound will pass through a treatment system, into the surrounding surface water and become part of the available water supply without substantial bacteriological degradation necessitates rejection of that compound for use in a detergent formulation.

The present invention meets both of these criteria and provides a biodegradable detergent builder which when incorporated into a formulation results in excellent detergent efficiency. As will now be described, the present invention is the discovery that certain acrylate polymers have unique and excellent detergent building properties. The particular acrylate polymers found useful are those having an average molecular weight of between about 500 and about 10,000, preferably less than 5000 and in the most preferred form, less than about 3000. At these levels the acrylate is more properly referred to as an "oligomer" rather than a "polymer" and will be so referred hereinafter.

Exerimentation with these compounds has shown that the chain terminating moiety plays an important part in both the building ability of the polyacrylate and in the relative ease of biodegradability. Although any chain terminating or chain transfer agent which will reasonably function with polyacrylate and does not impair biodegradability of the molecule may be used, such as alkyls, substituted alkyls, hydrogen and the residue from a free radical initiator, the preferred embodiments utilize compounds which will terminate at least one end of the chain with a sulfur containing moiety or an hydroxy containing moiety.

Examples of the type of compounds which can terminate a polyacrylate chain with either an hydroxy and/or a sulfur containing group include, but are not limited to, alkanols preferably having from one to six carbon atoms, glycols, glycol esters, glycolic acids and salts thereof, thiols having from one to twenty carbon atoms, thio carboxylic acids having at least one carboxylic group and salts thereof, thio alkanols and hydroxy substituted thiols. Although the mechanism and reasons are not completely understood, hydroxy and sulfur containing moietys, particularly sulfur containing moietys at the ends of the oligomeric polyacrylates of the present invention, enables use of lower concentrations of the detergent formulation in the wash solution than does an otherwise terminated acrylate without any impairment of detergent efficiency. In addition, these terminating groups are preferred because they permit use of lower weight and, therefore, more biodegradable oligomers than do other end caps to obtain the same relative building ability in the detergent formulation.

Preferred cations for the acrylate salts are the alkali metals, ammonium and substituted ammonium such as morpholinium, alkyl ammonium, mono-, di-, and trialkanol ammonium and tetra alkyl ammonium. It should be understood that the term polyacrylates, as used herein, includes within the defination, as an integral part thereof, polyalkylacrylates of from one to six carbon atoms; these also being considered efficacious as detergent builders. In this regard, the lower members of the group, i.e, methyl, ethyl and propyl acrylates are the most responsive to the needs of a detergent formulation. It should also be understood at this juncture that the term polyacrylates refers to acrylate homopolymers, acrylate copolymers and terpolymers, etc. wherein the acrylate moiety comprises at least 45 mole percent of the molecule.

The unique compounds found suitable for the present invention may thus be summerized by the general formula:

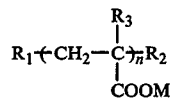

wherein n is a series of whole number integers such that the average molecular weight is less than about 10,000 preferably less than about 5000; $R_1$ and $R_2$ are moieties which do not impair biodegradability of the molecule such as, for example, alkyls, substituted alkyls, hydrogen, the residue from a free radical initiator, alkanols preferably having one to six carbon atoms, glycols, glycol esters, glycolic acids and salts thereof, thiols having from one to twenty carbon atoms, thio carboxylic acids having at least one carboxylic group and salts thereof, thio alkanols and hydroxy substituted thiols; $R_3$ is selected from the group consisting of hydrogen and alkyls having from one to six carbon atoms; and, M is selected from the group consisting of alkali metals, ammonium and substituted ammonium cations.

The weight ratio of the builder compounds of the present invention to detergent compound when used in laundering and hand dishwashing compositions, ranges generally from about 1:20 to about 20:1. When the novel builders are used in mechanical dishwashing compositions, the ratio of builder to detergent compound is from about 10:1 to about 50:1.

Builder compounds of the present invention can be used either as the sole builder or where desired can be used in conjunction with other builders, examples of which include the alkali metal salts of carboxymethyloxysuccinic acid and oxydiacetic acid, tetrasodium and tetrapotassium pyrophosphate, pentasodium and pentapotassium tripolyphosphates, ether polycarboxylates, citrates, starch or cellulose derived polycarboxylates, and the like. Other materials which may be present in the detergent compositions of the invention are those conventionally present therein. Typical examples thereof include soil suspending agents, hydrotropes, corrosion inhibitors, dyes, perfumes, fillers, abrasives, optical brighteners, enzymes, suds boosters, suds depressants, germicides, anti-tarnishing agents. cationic detergents, softeners, chlorine releasing agents, buffers and the like. The balance of the detergent compositions is water.

The detergent compositions of the present invention may be in any of the usual physical forms for such compositions, such as powders, beads, flakes, bars, tablets, noodles, liquids, pastes, and the like. The detergent compositions are prepared and utilized in the conventional manner.

When using the detergent compositions of the invention to wash clothes, the wash solutions should have a pH from about 7 to about 12, preferably from about 9 to 11. Therefore, the presence of a buffer in the detergent composition is usually desirable. Examples of such buffers are sodium silicate, carbonate or bicarbonate.

When the pH value of the wash solution is below about 8.6 some of the salts of the builder compounds will be present in the acid salt form and some in the normal salt form.

It should also be noted that when the compounds of the present invention are employed as the free acids or as partly neutralized salts, the compounds have utility in metal cleaning compositions under pH conditions of about 2 to about 5.

The following examples demonstrate without limiting the present invention preparation of low molecular weight polyacrylates suitable for use in detergent formulations, demonstrates their efficacy as detergent builders and their biodegradability.

EXAMPLE I

A screw cap flask is charged with 80g. water, 20g. isopropanol, 1.7g of 30% hydrogen peroxide and 10g. of glacial acrylic acid. The reaction solution is then heated at 83° C. for 67 hours. After cooling the remaining peroxide is destroyed using Pt foil as a catalyst. After evaporation of the solvents the polymeric residue is purified by dissolving in ethanol and precipitating with 2-butanone. The filtered product is then dried in a high vacuum drying pistol. A molecular weight determination using Vapor Phase Osmometry gives a value of ~10,270.

EXAMPLE II

The preparation described for Example I is repeated except that the reacting solution contains 70g. of water, 30g. isopropanol, 2.3g. of 30% hydrogen peroxide and 10g. of glacial acrylic acid. The average molecular weight of the oligomer obtained is ~3000.

EXAMPLE III

The preparation described for Example II is repeated except that 30g. of ethyl glycolate is used in place of the isopropanol as the chain transfer agent and the reaction time is 19 hours. The molecular weight of the purified oligomer is ~2000 as determined by Vapor Phase Osmometry.

EXAMPLE IV

A solution of 300 ml. of isopropanol containing 10g. of acrylic acid is heated to reflux. Then, 0.75g. of azo-bis-isobutyronitrile (AIBN) is added and the resulting solution, refluxed for 1 hour. The reaction mixture is then added to 800 ml of benzene and the resulting solution concentrated to 200 ml. The precipitated polymer is separated by centrifuging and dried in a vacuum oven at 55° C. in the presence of $P_2O_5$; the yield is 5.1g. The average molecular weight of the product as determined by Vapor Phase Osmometry is ~1050.

EXAMPLE V

The sodium salts of the above oligomeric polyacrylic acids are prepared by dissolving the oligomer in water and neutralizing with dilute solium hydroxide to pH = 8.6. The solution is then evaporated to dryness to recover the dry solid sodium salt.

EXAMPLE VI

A solution of acrylic acid, AIBN and n-dodecyl mercaptan in 300ml of methanol is refluxed for 2 hours. The reaction mixture is then concentrated to about 50 ml by evaporation in vacuo. Benzene, 100 ml, is then added whereby a lower oily layer is separated. After decanting the upper benzene layer, the lower layer is dissolved in 20 ml of methanol and treated again with benzene to separate a lower layer containing the oligomer. After repeating the purification step once more, the oily layer is evaporated in vacuo and the residue dried in a vacuum oven (50° C.) over $P_2O_5$. The average molecular weight of the product is determined by Vapor Phase Osmometry. Using the above procedure the following oligomeric polyacrylic acids end-capped with dodecyl mercaptan have been prepared:

| Example | Amount used, g./10g. acrylic acid | | Yeild(g.) | Average Molecular Weight |
|---|---|---|---|---|
| | Dodecyl Mercaptan | AIBN | | |
| VII | 3.0 | 2.0 | 6.0 | 1113 |
| VIII | 0.5 | 0.75 | 5.7 | 2250 |
| IX | 0.25 | 0.75 | 5.8 | 2520 |
| X | 0.10 | 0.75 | 6.3 | 2230 |

The sodium salts of the above oligometric polyacrylic acids are readily prepared by dissolving the oligomer in water and neutralizing to pH 8.6 with dilute sodium hydroxide. The resulting solution is then evaporated to dryness to recover the solid sodium salt.

EXAMPLES XI – XXIV

Detergent formulations were prepared utilizing 50 weight percent of the sodium salts of the above prepared polyacrylic acids in combination with 18 weight percent LAS, an anionic surfactant which is sodium linear secondary alkyl ($C_{10}$–$C_{15}$) benzene sulfonate, 10 weight percent of RU silicate solids, a sodium silicate having an $SiO_2$:$N_2O$ ratio of 2.4:1 and 22 weight percent water. A control formulation was prepared, for purposes of comparison, of 18 weight percent LAS, 50 weight percent of pentasodium tripolyphosphate as the builder, 10 weight percent RU silicate solids and 22 weight percent water.

Detergency building properties were measured with a Terg-O-Tometer test using a 65% Dacron-35% cotton cloth soiled with vacuum cleaner dust. The wash solution contained 180 ppm, 2:1 $Ca^{++}$/$Mg^{++}$, had an initial pH of 10, adjusted with dilute sodium hydroxide, and was maintained at a temperature of 120° F. Test concentrations of detergent formulations in the wash solution were 0.1 and 0.2 percent. The average detergency units (DU) of the formulations is the final reflectance of the washed cloth minus the initial reflectance of the solid cloth (the average of two runs), the reflectance being measured on a Gardner automatic color difference meter, Model AC-3. Table I summarizes the results:

TABLE I

| Example | Preparation Example | Average Molecular Weight | Formulation Concentration | Detergency Units (DU) | | % Efficiency $\frac{\text{Experimental DU}}{\text{Control DU}} \times 100$ |
|---|---|---|---|---|---|---|
| | | | | Experimental Formulation | Control Formulation | |
| XI | I | 10,270 | 0.1 | 25.5 | 25.5 | 100 |
| XII | I | 10,270 | 0.2 | 28.7 | 29.0 | 99 |
| XIII | II | 3,000 | 0.1 | 24.2 | 25.3 | 95 |
| XIV | II | 3,000 | 0.2 | 26.5 | 27.4 | 97 |
| XV | III | 2,000 | 0.1 | 22.8 | 24.1 | 95 |
| XVI | III | 2,000 | 0.2 | 26.7 | 26.6 | 100 |
| XVII | IV | 1,050 | 0.1 | 19.5 | 27.1 | 72 |
| XVIII | IV | 1,050 | 0.2 | 28.7 | 29.1 | 98 |
| XIX | VII | 1,113 | 0.1 | 25.5 | 26.7 | 96 |
| XX | VII | 1,113 | 0.2 | 28.3 | 29.3 | 97 |
| XXI | VIII | 2,250 | 0.1 | 24.9 | 26.7 | 93 |
| XXII | VIII | 2,250 | 0.2 | 27.4 | 29.3 | 94 |
| XXIII | IX | 2,520 | 0.1 | 25.1 | 26.7 | 94 |
| XXIV | IX | 2,520 | 0.2 | 28.0 | 29.3 | 96 |

As can be seen from the data of Table I, the oligomeric polyacrylate built detergents according to the present invention compare quite favorably with the phosphate built detergent control. The test results clearly show that within the most preferred range of the present invention, i.e., an average molecular weight of between about 500 and 3000, thiol end-capped polyacrylate can be successfully used as a phosphate replacement at both the 0.1 and 0.2 percent wash solution concentrations; hydroxy end-capped polyacrylate also performs very well at the 0.1 and 0.2 percent concentrations at average molecular weight of 2000 and 3000 but begins to show signs of strain at the 0.1 percent concentration for the 1050 molecular weight. Note should be taken, however, that the 0.2 percent concentration of 1050 molecular weight polyacrylate built detergent resulted in 98 percent efficiency which can be considered as excellent. Further testing with the very low molecular weight 1050 builders of the present invention at 0.1 percent concentrations determined that when the presence of the anionic surfactant was boosted from 18 to 36 percent, the amount of builder and RU silicate remaining constant, the efficiency increased to a very acceptable 93 percent.

Table II summarizes results obtained at formulation concentrations in wash solution of 0.15 percent with various detergent compositions. In all cases the sodium salt of the polyacrylic acid was used and the same Terg-O-Tometer conditions of test material and hardness, temperature and pH as in the above examples, were observed. STPP is pentasodium tripolyphosphate; RU silicate solids is a sodium silicate having an $SiO_2:Na_2O$ ratio of 2.4:1; Tergitol 15-S-7 is an adduct of seven moles of ethylene oxide per mole of a random secondary alcohol derived from $C_{11-15}$ normal parafins; $C_{14-16}$ HAMT is an ampholytic surfactant which is sodium-N-2 hydroxy $C_{14-16}$ alkyl-N-methyltaurate; and, Sulfobetaine DCH is a zwitterionic surfactant which is cocodimethylsulfopropylbetaine.

TABLE III

| Preparation | Ex. | Molecular Weight | Average BOD | | COD | BOD as % of COD |
|---|---|---|---|---|---|---|
| | I | 10,270 | 17 | (5 Day) | 1323 | 13 |
| | II | 3,000 | 96 | " | 1432 | 22 |
| | III | 2,000 | 103 | " | 1344 | 25 |
| | IV | 1,050 | 139 | " | 1407 | 30 |
| Acrysol A-1 | | <50,000 | 51 | " | 1340 | 13 |
| | VII | 1,113 | 229 | (21 Day) | 1488 | 54 |
| Acrysol A-1 | | <50,000 | 65 | " | 1340 | 16.4 |

BOD values are basis 300 mg. solids; COD values are basis 1000 mg solids.

$$\text{BOD as a \% of COD is determined by } \frac{\frac{BOD}{300}}{\frac{COD}{1000}} \times 100$$

The above figures clearly indicate that the novel polyacrylate oligomers of the present invention have noticeably improved biodegradability over 5 days and excellent biodegradability over 21 days relative to the higher molecular weight polymers. Careful note should be taken that the product of Preparation Example I having a molecular weight of 10,270 had a very poor biodegradability over five days and, in fact, would be classified as non-degradable. For purposes of further comparison, a commercially available polyacrylate, Acrysol A-1 marketed by Rohm & Haas, having an average molecular weight of less than 50,000 was tested as above for five days and twenty-one days. The BOD as a percentage of COD for five days was between about 0 and about 13 percent and for twenty-one days was 16.4 percent, which would also classify this material as non-degradable.

TABLE II

| | Examples XXV – XXXII, Percentages by Weight | | | | | | | |
|---|---|---|---|---|---|---|---|---|
| | XXV | XXVI | XXVII | XXVIII | XXIX | XXX | XXI | XXXII |
| 1. Preparation Example VII | 50 | — | — | — | — | — | — | — |
| 2. Preparation Example VIII | — | — | 50 | — | — | — | — | — |
| 3. Preparation Example IX | — | — | — | — | 50 | — | — | — |
| 4. Preparation Example X | — | — | — | — | — | — | 50 | — |
| 5. STPP | — | 50 | — | 50 | — | 50 | — | 50 |
| 6. RU Silicate Solids | 10 | 10 | 10 | 10 | 10 | 10 | 10 | 10 |
| 7. Sodium $C_{15-18}$ α-olefin sulfonate | 18 | 18 | — | — | — | — | — | — |
| 8. Tergitol 15-S-7 | — | — | 10 | 10 | — | — | — | — |
| 9. $C_{14-16}$ HAMT | — | — | — | — | 18 | 18 | — | — |
| 10. Sulfobetaine DCH | — | — | — | — | — | — | 18 | 18 |
| 11. Water | ← | ← | ← | balance | to 100% | → | → | → |
| Detergency, DU's | 24.5 | 27.4 | 27.7 | 28.8 | 26.7 | 28.4 | 29.0 | 29.9 |
| % Efficiency compared to control formulation (i.e., XXV vs. XXVI, XXVII vs. XXVIII, XXIX vs. XXX, XXXI vs. XXXII) | 90 | | 97 | | 94 | | 97 | |

As can be seen from the data in Table II, particularly the comparisons in the last line between the detergents built according to the present invention and the similarly constituted but phosphate built detergent controls, the efficiency is at least 90 percent and reaches as high as 97 percent which can be considered as very favorable. Thus, at the 0.15 percent wash concentrations, which is the level normally practiced in this country, the detergents built according to the present invention are adjudged to be excellent phosphate replacements.

Several of the oligomeric polyacrylates prepared in the above Example were then tested for biodegradability using either five day or twenty-one day BOD testing. Table III shows this data as well as chemical oxygen demand (COD) and the BOD as a percentage of COD.

Thus, it can b readily appreciated from each of the foregoing tables that this discovery of a novel class of polyacrylates which have both high biodegradability and excellent detergent building properties answers a long felt need in the art for a phosphorus free oligomeric builder.

As this invention may be embodied in several forms without departing from the spirit or essential character thereof, the present embodiments are illustrative and not restrictive. The scope of the invention is defined by the appended claims rather than by the description preceding them and all embodiments and formulations which fall within the meaning and range of equivalency of the claims are, therefore, intended to be embraced by those claims.

We claim:

1. An oligomeric polyacrylate having an average molecular weight of greater than 500 and less than about 10,000 and a formula represented by:

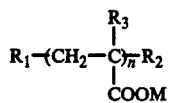

wherein n is a whole number integer, $R_1$ and $R_2$ are moieties which do not impair biodegradability of the molecule and are selected from the group consisting of hydrogen, alkanols having from one to six carbon atoms, glycols, glycol esters, glycolic acids and salts of glycolic acids, $R_3$ is selected from the group consisting of hydrogen and alkyl groups having from one to six carbon atoms and M is selected from the group consisting of hydrogen, alkali metals, ammonium and substituted ammonium cations.

* * * * *

UNITED STATES PATENT OFFICE
CERTIFICATE OF CORRECTION

Patent No. 4,132,735           Dated January 2, 1979

Inventor(s) Vincent Lamberti, et al

It is certified that error appears in the above-identified patent and that said Letters Patent are hereby corrected as shown below:

The portion of the term of this patent subsequent to

June 13, 1995, has been disclaimed.

Signed and Sealed this

Tenth Day of April 1979

[SEAL]

Attest:

RUTH C. MASON
Attesting Officer

DONALD W. BANNER
Commissioner of Patents and Trademarks